United States Patent
Repicci

(10) Patent No.: US 6,726,724 B2
(45) Date of Patent: Apr. 27, 2004

(54) PROSTHETIC KNEE

(76) Inventor: John A. Repicci, 120 Deer Run, Williamsville, NY (US) 14221

( * ) Notice: Subject to any disclaimer, the term of this patent is extended or adjusted under 35 U.S.C. 154(b) by 12 days.

(21) Appl. No.: 10/143,284

(22) Filed: May 10, 2002

(65) Prior Publication Data

US 2002/0133230 A1 Sep. 19, 2002

Related U.S. Application Data

(63) Continuation of application No. 09/748,425, filed on Dec. 26, 2000, now Pat. No. 6,503,280.

(51) Int. Cl.$^7$ ................................................ A61F 2/38
(52) U.S. Cl. .................................. 623/20.29; 623/20.33
(58) Field of Search ....................... 623/14.12, 20.21, 623/20.23, 20.28, 20.29, 20.32, 20.33

(56) References Cited

U.S. PATENT DOCUMENTS

| | | | |
|---|---|---|---|
| 3,688,316 A | 9/1972 | Lagrange et al. | |
| 3,848,276 A | 11/1974 | Martinez | |
| 4,001,896 A | 1/1977 | Arkangel | |
| 4,085,466 A | 4/1978 | Goodfellow et al. | |
| 4,213,209 A | 7/1980 | Insall et al. | |
| 4,568,348 A | 2/1986 | Johnson et al. | |
| 4,586,933 A | 5/1986 | Shoji et al. | |
| 4,731,086 A | 3/1988 | Whiteside et al. | |
| 4,865,606 A * | 9/1989 | Rehder ........................ | 623/20 |
| 4,964,868 A | 10/1990 | Bloebaum | |
| 4,979,957 A | 12/1990 | Hodorek | |
| 5,059,216 A | 10/1991 | Winters | |
| 5,171,276 A | 12/1992 | Caspari et al. | |
| 5,192,328 A | 3/1993 | Winters | |
| 5,207,711 A | 5/1993 | Caspari et al. | |
| 5,219,362 A | 6/1993 | Tuke et al. | |
| 5,312,254 A * | 5/1994 | Rosenlicht ................... | 433/173 |
| 5,330,534 A | 7/1994 | Herrington et al. | |
| 5,336,366 A | 8/1994 | Cain et al. | |
| 5,358,529 A | 10/1994 | Davidson | |
| 5,658,342 A | 8/1997 | Draganich et al. | |
| 5,683,467 A | 11/1997 | Pappas | |
| 5,728,162 A | 3/1998 | Eckhoff | |
| 5,824,101 A | 10/1998 | Pappas | |

(List continued on next page.)

FOREIGN PATENT DOCUMENTS

| | | |
|---|---|---|
| EP | 0346183 | 5/1988 |
| FR | 2685632 | 12/1991 |
| FR | 2691356 | 5/1992 |
| FR | 2750036 | 6/1996 |
| WO | PCT/US89/00387 | 1/1989 |

OTHER PUBLICATIONS

European Search Report.
Abstract.

*Primary Examiner*—Eduardo C. Robert
*Assistant Examiner*—Anuradha Ramana
(74) *Attorney, Agent, or Firm*—Roach Brown McCarthy & Gruber, P.C.; Kevin D. McCarthy

(57) ABSTRACT

The present invention relates to a prosthetic knee. In one embodiment of the present invention, the knee has a femoral body and meniscal body. The femoral body has a femoral alignment member, and the meniscal body has a femoral side. Extending from the femoral side are at least two guiding protrusions that extend along the longitudinal axis of the meniscal body and define at least two sides of an alignment groove. The alignment groove slippingly receives the femoral alignment member. The femoral alignment is able to move within the alignment groove and slip over the alignment groove when a force of sufficient magnitude is applied to the prosthetic and revert into the alignment groove. In another embodiment of the present invention, the groove and the alignment components are reversed on the respective femoral and meniscal bodies.

9 Claims, 2 Drawing Sheets

U.S. PATENT DOCUMENTS

| | | | |
|---|---|---|---|
| 5,879,392 A | * | 3/1999 | McMinn ..................... 623/20 |
| 5,906,643 A | | 5/1999 | Walker |
| 5,997,577 A | | 12/1999 | Herrington et al. |
| 6,004,351 A | | 12/1999 | Tomita et al. |
| 6,019,794 A | | 2/2000 | Walker |
| 6,102,955 A | | 8/2000 | Mendes et al. |
| 6,171,340 B1 | | 1/2001 | McDowell |
| 6,264,697 B1 | | 7/2001 | Walker |
| 6,346,110 B2 | * | 2/2002 | Wu ............................. 606/108 |
| 6,503,280 B2 | * | 1/2003 | Repicci ................... 623/20.14 |

\* cited by examiner

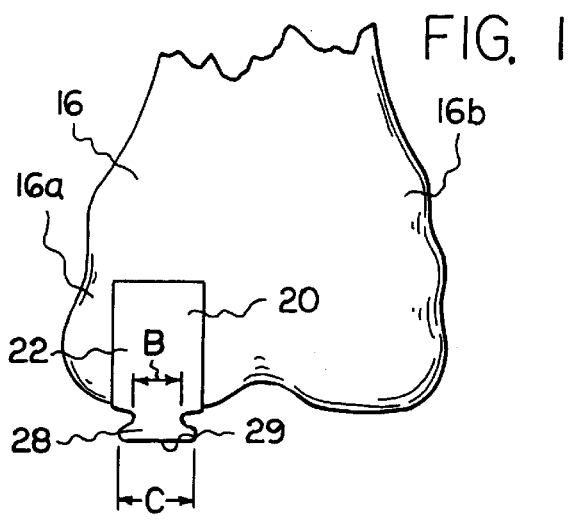
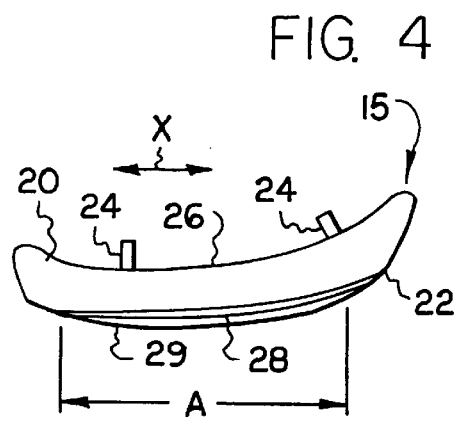
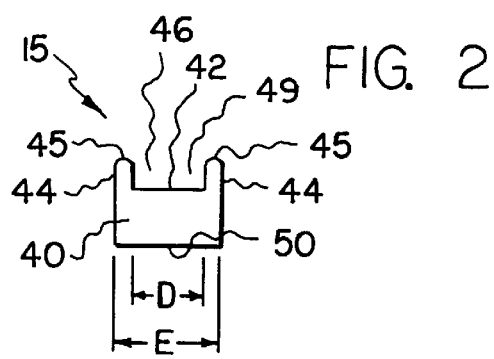
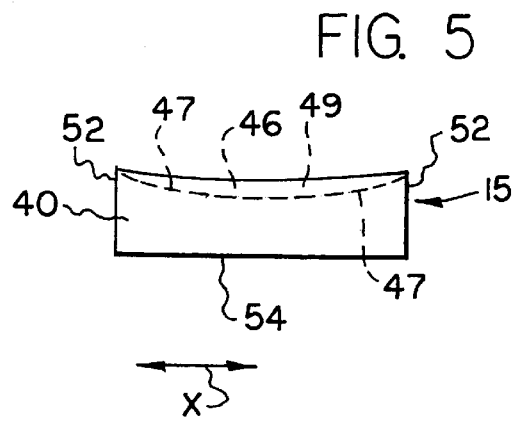
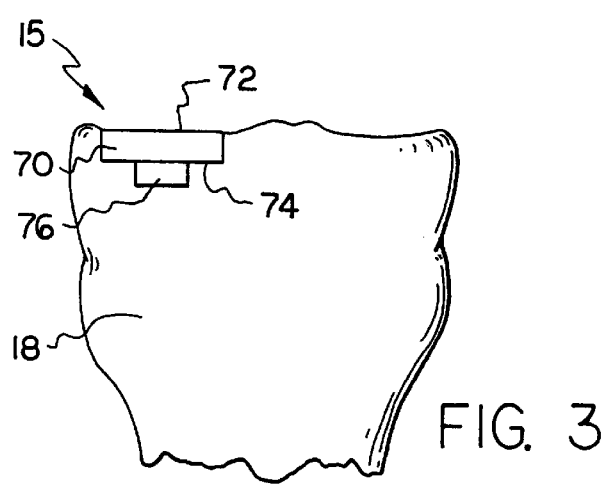
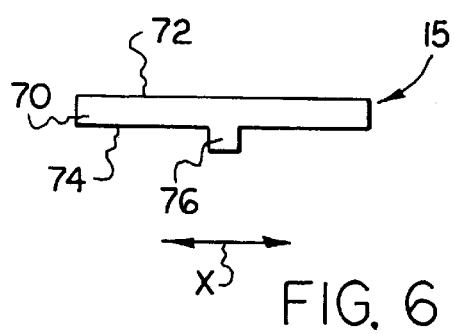

PROSTHETIC KNEE

CLAIM OF PRIORITY

This application is a continuation to U.S. patent application Ser. No. 09/748,425 (filed Dec. 26, 2000) now U.S. Pat. No. 6,503,280.

FIELD OF THE INVENTION

The present invention relates to a prosthetic device and more particularly to a prosthetic knee.

BACKGROUND OF THE INVENTION

The human knee is a complex arrangement of ligaments, cartilages, and bone surfaces. The human knee is a versatile component that when properly operating can withstand various loads and forces being applied to it. When such various forces are applied, the knee adapts and moves in relation to those forces.

However, because the knee is subjected to great loads and tremendous use, the knee is subject to a host of different ailments, all of which result in discomfort and pain. Osteoarthritis, for example, commonly occurs in older people, and is typically found in the weight bearing joints of a human body, such as the knee and the hip. When osteoarthritis effects a knee, the articular cartilage of the knee degenerates, and the femur and tibia typically begin to wear against one another. This results in pain and stiffness in the joint, and makes flexion and extension of the knee difficult. People suffering this condition are often unable to partake in even the simplest physical activities.

Also, injuries to the articular cartilages of the knee often may arise from any of a plurality of sporting activities, like jogging and skiing, that exert substantial forces on the knee. Additionally, accidents and falls apply substantial forces to a knee. Such substantial forces may result in the damage or destruction of the articular cartilages in the knee.

Several prosthetic devices are presently available to assist individuals with knee ailments. These devices, however, have shortcomings, such as when loads and forces are applied to the components of the prosthetic some of the components slip away from each other. When such slippage occurs, the conventional prosthetic knee has difficulty joining the components together. For example, in one embodiment of a prosthetic knee the components lock together by a tongue and grove system. In another embodiment of a prosthetic knee, the components contact each other on curved and/or flat surfaces. When these components disengage from each other, they are difficult to mate together. The present invention allows some slippage and simultaneously corrects the slippage.

SUMMARY OF THE INVENTION

The present invention relates to a prosthetic knee. In one embodiment of the present invention, the knee has a femoral body and a meniscal body. The femoral body has a femoral alignment member, and the meniscal body has a femoral side. Extending from the femoral side are at least two guiding protrusions that extend along the longitudinal axis of the meniscal body and define at least two sides of an alignment groove. The alignment groove slippingly receives the femoral alignment member. The femoral alignment is able to move within the alignment groove and slip over the alignment groove when a force of sufficient magnitude is applied to the prosthetic and revert into the alignment groove. In another embodiment of the present invention, the groove and the alignment components are reversed on the respective femoral and meniscal bodies.

BRIEF DESCRIPTION OF THE DRAWINGS

FIG. 1 shows a front elevational view of the femoral body of the prosthetic knee.

FIG. 2 shows a front elevational view of the meniscal body of the prosthetic knee.

FIG. 3 shows a front elevational view of the tibial body of the prosthetic knee.

FIG. 4 shows a side elevational view of the femoral body of the prosthetic knee.

FIG. 5 shows a side elevational view of the meniscal body of the prosthetic knee.

FIG. 6 shows a side elevational view of the tibial body of the prosthetic knee.

DETAILED DESCRIPTION

Figure 7:
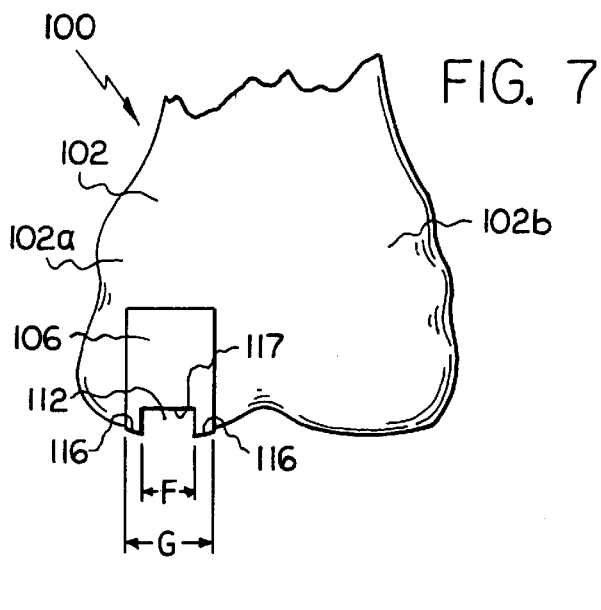
FIG. 7 shows a front elevational view of an alternate embodiment of the femoral body of the prosthetic knee.

The present invention relates to a prosthetic half knee 15, which is embodied in FIGS. 1–6. The knee 15 comprises three major components: a femoral body 20, a meniscal body 40, and a tibial body 70. The femoral body 20 is attached to the femur 16 by at least one femur anchor post 24 as shown in FIG. 4. The femur anchor post 24 may be cemented to or driven into the femur 16 using processes and materials well known to those skilled in the art. Similarly, as illustrated in FIGS. 3 and 6, the tibial body 70 is attached to the tibia 18 by at least one tibia anchor post 76. This may be accomplished by cementing or driving the anchor posts 76 to the tibia 18, or by other processes well known to those skilled in the art. Interposed between the femoral body 20 and the tibial body 70 is the meniscal body 40, illustrated in FIGS. 2 and 5.

The femoral body 20 is constructed in an convex arcuate shape such that it is in the condylic shape of a natural femur bone. It may be made of durable plastic or metal, but in either case, materials with low coefficients of friction will prolong the useful life of the prosthetic knee, and facilitate walking and other endeavors. The selection of such materials for such purposes are well known to those skilled in the art. Protruding from the femoral body contact surface 26 is the at least one femur anchor post 24, which anchors the femoral body 20 to the femur 16 as described above. In other embodiments of the present invention, the femoral body 20 may be attached to the femoral bone by making a plurality of holes (not shown) in the contact surface 26 and allowing the bone of the femur 16 to grow therein.

The femoral body 20 has a convex arcuate surface 22 spanning its longitudinal axis, this being a load bearing surface supporting loads transmitted from the femur 16. The femoral body 20 has mergedly rising from its convex arcuate surface 22 and spanning a portion thereof designated by line segment A—A in FIG. 4, the femoral alignment member 28, shown in FIG. 1. The femoral alignment member 28 has a sliding surface 29. The femoral alignment member 28 is shaped such that the span of its narrowest width, designated by line segment B—B in FIG. 1, is less than the span of its greatest width, designated by line segment C—C in FIG. 1. This configuration is further described below.

Turning now to FIGS. 2 and 5, shown therein are front and side elevational views of the meniscal body 40. The meniscal body has a femoral side 42, a tibial side 50, and guiding protrusions 44. The guiding protrusions 44 extend from the femoral side 42 of the meniscal body 40. The guiding protrusions 44 have tapered, rounded, or beveled end portions 45.

Defined between the guiding protrusions 44 is the alignment groove 46, shown in FIGS. 2 and 5. The alignment groove 46 spans the meniscal body 40 along the longitudinal X axis direction, as shown in FIG. 2. The meniscal body 40 is embodied between the guiding protrusions, and is less than the distance between the guiding protrusions 44, designated by line segment E—E in FIG. 2. As shown, the protrusions can have extensions that secure, with some slippage movement allowed between the meniscal body and the alignment groove. Alternatively, there could be no extensions which also allow the meniscal body and alignment groove to move within.

The alignment groove 46 may be embodied to span the length of the meniscal body 40, and be further embodied such that the depth 49 of the alignment groove 46 varies along the longitudinal X axis thereof. In such an embodiment, as shown in FIG. 4, the depth 49 of the alignment groove 46 is, in the preferred embodiment, greater at the center portion 54 of the meniscal body 40, than the depth 49 at the ends 52 of the meniscal body 40. In such an embodiment, the alignment groove 46 may have a generally concave curvature 47 along the longitudinal X axis of the meniscal body 40. The meniscal body 40 itself is embodied to have a concave shape along its longitudinal X axis, shown in FIG. 5. The meniscal body 40 may be constructed of durable plastic, metal, or other materials well known to those skilled in the art.

FIGS. 3 and 6 show the tibial body 70, which has a support surface 72 that supports the meniscal body 40. The tibial body 70 also has a support surface 74 which rests on the tibia 18. The tibial body 70 is anchored to the tibia 18 by the tibial body anchor posts 76. The tibial body 70 may be constructed of hard durable plastic, metal, or other materials well known to those skilled in the art. The tibial body 70 may be cemented to the tibia 18 with adhesives and cements known to those skilled in the art. The tibial body 70 may also be constructed with a plurality of holes (not shown), such that the tibia 18 bone grows into the holes and attaches itself to the tibial body 70 in that manner.

The femoral body 20, the meniscal body 40, and the tibial body 70 are constructed as described above and are inserted into a patient by procedures well known to those skilled in the art. The femur 16 and the tibia 18 are prepared for receiving the prosthetic 15. This process typically entails shaping the femur 16 and tibia 18 such that they are altered, for example flattened in some embodiments or rounded in other embodiments (not shown), to receive the femur anchor posts 24 and the tibial body anchor posts 76. The femur anchor posts 24 and tibial body anchor posts 76 are driven into the femur 16 and tibia 18 respectively.

The meniscal body 40 is slid over the femoral alignment member 28 along the sliding surface 29. In this position, the femoral alignment member 28 occupies and is received in the alignment groove 46 in the meniscal body 40. The femoral alignment member 28 is captured in the alignment groove 46. Thus, as the prosthetic knee 15 articulates back and forth in the X axis direction, shown in FIGS. 4–6, the femoral alignment member 28 slides back and forth along the alignment groove 46. The lack of any extensions from the guiding extensions allow the femoral body 20 to slip out of the alignment groove 40 and on to a wall of the guiding extension in such a way that the femoral body 20 is able to revert into the alignment groove 40 without difficulty, and, hopefully, naturally. As stated previously, forces are applied to a knee. The present invention allows the knee to receive forces and loads from various angles. And when the knee receives a force or load other than one at 0° relative to the femur and/or the tibia, the present invention allows the prosthetic knee to accommodate and adapt to those forces and/or loads without having the knee being damaged. This arrangement allows the user maximum possible flexion and extension capabilities in the knee, without problems of the meniscal body 40 undesirably and permanently slipping and sliding out of the X axis direction of travel without extraordinary forces being applied thereon.

To achieve the proper tension in the prosthetic knee 15 during flexion and extension thereof, the meniscal body 40 thickness may need to be adjusted. For each differently sized individual, a meniscal body 40 of different thickness may be selected. Such sizing of prosthetics to patients is well known to those skilled in the art.

Figure 10:
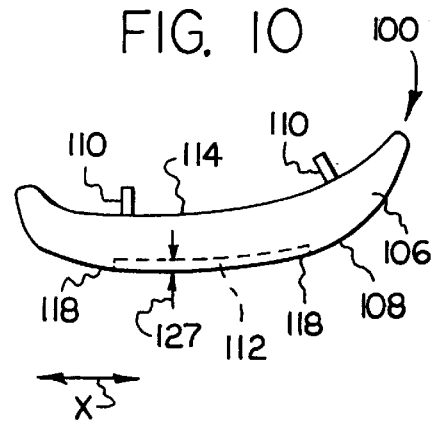
FIG. 10 shows a side elevational view of an alternative embodiment of the femoral body of the prosthetic knee.
Figure 8:
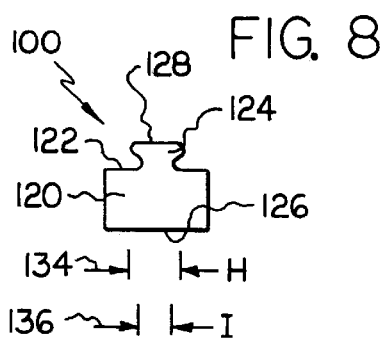
FIG. 8 shows a front elevational view of an alternative embodiment of the meniscal body of the prosthetic knee.
Figure 11:
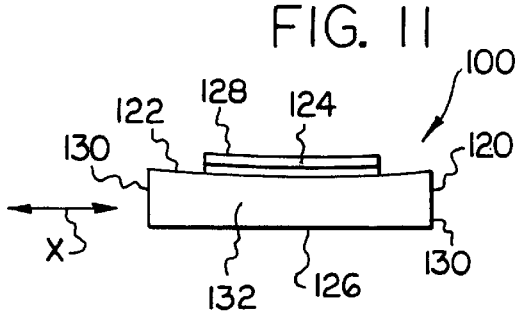
FIG. 11 shows a side elevational view of an alternative embodiment of the meniscal body of the prosthetic knee.
Figure 9:
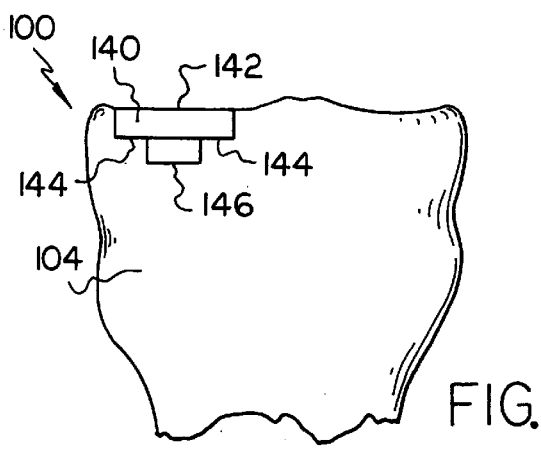
FIG. 9 shows a front elevational view of an alternative embodiment of the tibial body of the prosthetic knee.
Figure 12:
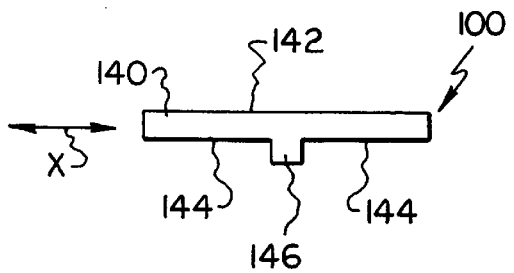
FIG. 12 shows a side elevational view of an alternative embodiment of the tibial body of the prosthetic knee.

Another embodiment of the prosthetic knee 15, illustrated in FIGS. 7–12, comprises three major components: a femoral body 106, a meniscal body 120, and a tibial body 140. The femoral body 106 is attached to the femur 102 by at least one femur anchor post 110, extending from the femoral body bone contact surface 114, as shown in FIGS. 7 and 10. The femur anchor posts 110 may be cemented to or driven into the femur 102 using processes and materials well known to those skilled in the art. Similarly, as illustrated in FIGS. 9 and 12, the tibial body 140 is attached to the tibia 104 by at least one tibia anchor post 146. This may be accomplished by cementing the tibia anchor posts 146 to the tibia 104 or by other processes well known to those skilled in the art. Interposed between the femoral body 106 and the tibial body 140 is the meniscal body 120, as illustrated in FIGS. 7–9.

Referring to FIGS. 7 and 10, the femoral body 106 is shown, having a convex arcuate surface 108 spanning its longitudinal axis in the X direction, this being a load bearing surface. The convex arcuate surface 108 has a femoral body alignment cutout 112 extending along a portion of the longitudinal axis thereof, illustrated in FIGS. 7 and 10. The femoral body alignment cutout 112 is defined by the femoral guides 116. The femoral alignment cutout 112 being shaped such that the distance between the distance between the femoral guides 116, indicated by line segment F—F in FIG. 7, is equivalent to or less than the width of the sliding surface 117 of the femoral body 106, indicated by line segment G—G.

The depth 127 of the femoral alignment cutout 112, may be embodied to vary along the longitudinal X axis of the femoral body 106, such that at the ends of the cutout 118, the depth 127, is less than at the center portion 119, of the femoral body 106, as seen in FIGS. 7 and 10. The femoral alignment cutout 112 also may be embodied to have a convex curvature along its longitudinal X axis.

Referring to FIGS. 8 and 11, the meniscal body 120 has an alignment side 122, and extending from the alignment side 122 a meniscal alignment member 124. Opposite the alignment side 122 is the tibial side of meniscal body 126. The alignment member 124 has bearing surface 128 having a first width 134, indicated by line segment H—H in FIG. 8, which is greater than second width 136, designated line segment I—I in FIG. 8. Bearing surface 128 is in a sliding relationship with sliding surface 117 of the femoral body 106. The thickness of the meniscal body 120 may be embodied such that the thickness is greater at the end portions 130 of the meniscal body, than at the center portion 132, as shown in FIG. 11. This gives the meniscal body 120 a concave curvature along the longitudinal X axis direction, as depicted in FIG. 11.

The tibial body 140 shown in FIGS. 9 and 12, has on one side a support surface 142 for supporting the meniscal body 120, and on the other side a support surface 144 for resting on the tibia 104. The tibial body 140 may be constructed of hard durable plastic, metal, or other materials known to those skilled in the art. The tibial body 140 may be cemented to the tibia 104 with adhesives and cements known to those skilled in the art. The tibial body 140 may also be constructed with a plurality of holes such that the tibia bone 104 grows into the holes and attaches itself to the tibial body 140 in that manner.

The femoral body 106, the meniscal body 120, and the tibial body 140 are constructed as described above, and are inserted into a patient by procedures well known to those skilled in the art. The femur 102 and the tibia 104 are prepared for receiving the prosthetic. This process typically entails shaping the femur 102 and tibia 104 such that they are flattened to receive the femoral body anchor posts 110 and the tibial body anchor posts 146. Then, the femoral anchor posts and tibial body anchor posts 146 are driven into the femur 102 and tibia 104 respectively.

The meniscal alignment member 124 of the meniscal body 120 is slid into the femoral alignment cutout 112, and captured therein by the femoral guides 116. The meniscal body 120 and the femoral body 106 are thus able to slide relative to one another along the X axis direction, as shown in FIGS. 10–12. Further, since the alignment member 124 occupies the femoral alignment cutout 112, and is thus limited to motion in the X axis direction, the prosthetic knee 100 is stable during flexion and extension thereof.

Additionally, either embodiment of the prosthetic knee described herein may be used in conjunction with the medial condyle of the femur 16a and 102a, or the lateral condyle of the femur 16b and 102b, or both. Such procedures for implanting a prosthetic knee are well known to those skilled in the art.

The present invention can be distributed to medical practitioners through a kit. The kit contains the present invention in a sterile environment so the medical practitioner can open the kit in the operating room and use the prosthetic knee. The prosthetic knee, as stated earlier, is inserted into a patient through conventional methods known to those skilled in the art.

It will be understood that various changes in the details, materials, steps and arrangements of parts, which have been herein described and illustrated in order to describe the nature of the artificial knee, may be made by those skilled in the art within the principle and scope of the invention as expressed in the appended claims. For example, any of a plurality of differently shaped femoral alignment members 28 (rounded, squared, or beveled), and corresponding alignment grooves 46 (rounded, squared, or beveled) and guiding protrusions 44 are within the ambit of the prosthetic knee and appended claims. Additionally, any of a plurality of differently shaped femoral alignment cutouts 112, and corresponding meniscal alignment members 124 are within the ambit of the present prosthetic knee and appended claims.

What is claimed is:

1. A prosthetic comprising:
   a femoral body defining a femoral alignment cutout defined by at least two femoral guides from the femoral body on at least two sides of the femoral alignment cutout;
   a meniscal body having a bottom side and an alignment side, the bottom side is capable of being secured to a tibial body and the alignment side has a meniscal alignment member extending therefrom;
   the meniscal alignment member has a stem section and a bearing surface, the bearing surface (a) is capable of contacting the femoral alignment cutout and (b) has a greater width than the stem section; and
   the femoral alignment cutout able to slippingly receive and release the meniscal alignment member so the meniscal alignment member can move within the femoral alignment cutout and is also able to slip on to the femoral guides when a force of sufficient magnitude is applied to the prosthetic and reverts into the femoral alignment cutout.

2. The prosthetic of claim 1 wherein the femoral body has a sliding surface having a width, such that the distance between the femoral guides is less than the width of the sliding surface of the femoral body.

3. The prosthetic of claim 2 wherein the meniscal body has a bearing surface in a slidable relationship with the sliding surface of the femoral body.

4. The prosthetic of claim 3 wherein the bearing surface and the sliding surface are constructed of materials having low coefficients of friction.

5. A prosthetic comprising:
   a femoral body defining a femoral alignment cutout defined by at least two femoral guides from the femoral body on at least two sides of the femoral alignment cutout;
   a tibial body having a surface for support; and
   a meniscal body interposed between the tibial body and femoral body and situated on the surface for support, the meniscal body having a bottom side and an alignment side, the bottom side is capable of contacting the surface and the alignment side has a meniscal alignment member extending therefrom;
   the meniscal alignment member has a stem section and a bearing surface, the bearing surface (a) is capable of contacting the femoral alignment cutout and (b) has a greater width than the stem section; and
   the femoral alignment cutout able to slippingly receive and release the meniscal alignment member so the meniscal alignment member can move within the femoral alignment cutout and is also able to slip on to the femoral guides when a force of sufficient magnitude is applied to the prosthetic and reverts into the femoral alignment cutout.

6. The prosthetic of claim 5 wherein the femoral body has a sliding surface having a width, such that the distance between the femoral guides is less than the width of the sliding surface of the femoral body.

7. The prosthetic of claim 6 wherein the meniscal body has a bearing surface in a slidable relationship with the sliding surface of the femoral body.

8. A kit comprising (1) a prosthetic knee having
- a femoral body defining a femoral alignment cutout defined by at least two femoral guides from the femoral body on at least two sides of the femoral alignment cutout;
- a meniscal body interposed between the tibial body and femoral body and situated on the surface for support, the meniscal body having a bottom side and an alignment side, the bottom side is capable of being secured to a tibial body and the alignment side has a meniscal alignment member extending therefrom;
- the meniscal alignment member has a stem section and a bearing surface, the bearing surface (a) is capable of contacting the femoral alignment cutout and (b) has a greater width than the stem section; and
- the femoral alignment cutout able to slippingly receive and release the meniscal alignment member so the meniscal alignment member can move within the femoral alignment cutout and is also able to slip on to the femoral guides when a force of sufficient magnitude is applied to the prosthetic and reverts into the femoral alignment cutout; and (2) a kit that holds the prosthetic knee in a sterile environment.

9. A method of inserting a prosthetic knee into a mammal comprising the steps of:

inserting a femoral body defining a femoral alignment cutout defined by at least two femoral guides from the femoral body on at least two sides of the femoral alignment on a predetermined portion of a femur;

securing a meniscal body onto a tibial body wherein, the meniscal body having a bottom side and an alignment side, the bottom side is capable of being secured to the tibial body and the alignment side has a meniscal alignment member extending therefrom; the meniscal alignment member has a stem section and a bearing surface, the bearing surface (a) is capable of contacting the femoral alignment cutout and (b) has a greater width than the stem section; and wherein the prosthetic further has the femoral alignment cutout able to slippingly receive and release the meniscal alignment member so the meniscal alignment member can move within the femoral alignment cutout and is also able to slip on to the femoral guides when a force of sufficient magnitude is applied to the prosthetic and reverts into the femoral alignment cutout.

* * * * *